United States Patent
Fujimori

(10) Patent No.: US 11,109,749 B2
(45) Date of Patent: Sep. 7, 2021

(54) ENDOSCOPE

(71) Applicant: OLYMPUS CORPORATION, Tokyo (JP)

(72) Inventor: Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 403 days.

(21) Appl. No.: 15/958,063

(22) Filed: Apr. 20, 2018

(65) Prior Publication Data
US 2018/0303325 A1    Oct. 25, 2018

Related U.S. Application Data

(63) Continuation of application No. PCT/JP2016/081041, filed on Oct. 20, 2016.

(30) Foreign Application Priority Data

Oct. 27, 2015    (WO) .................. PCT/JP2015/080181

(51) Int. Cl.
*A61B 1/05*    (2006.01)
*G02B 23/24*    (2006.01)
(Continued)

(52) U.S. Cl.
CPC ............ *A61B 1/051* (2013.01); *A61B 1/0011* (2013.01); *A61B 1/0057* (2013.01);
(Continued)

(58) Field of Classification Search
CPC ... A61B 1/051; A61B 1/00096; A61B 1/0011; A61B 1/0017
See application file for complete search history.

(56) References Cited

U.S. PATENT DOCUMENTS 4,745,470 A * 5/1988 Yabe .................... H04N 5/2253
                                                               348/76
4,772,093 A * 9/1988 Abele ................ A61B 1/00096
                                                               385/117
(Continued)

FOREIGN PATENT DOCUMENTS

EP    2436300 A1    4/2012
EP    2614766 A1    7/2013
(Continued)

OTHER PUBLICATIONS

International Search Report dated Dec. 6, 2016 issued in PCT/JP2016/081041.

*Primary Examiner* — Alexandra L Newton
*Assistant Examiner* — Jae Woo
(74) *Attorney, Agent, or Firm* — Scully, Scott, Murphy & Presser, P.C.

(57) ABSTRACT

An endoscope includes an insertion portion that includes a distal end portion and a bending portion configured to change a direction of the distal end portion. The distal end portion includes a casing having a round shape in a cross-section, and an image pickup module that includes an optical module section including a plurality of optical members and an image pickup section, the image pickup module having a rectangular shape in a cross-section, and the image pickup section includes an image pickup device and a semiconductor stack in which a plurality of semiconductor devices is stacked, and entirety of the image pickup module is completely housed inside the casing.

9 Claims, 15 Drawing Sheets

(51) Int. Cl.
*A61B 1/04* (2006.01)
*A61B 1/00* (2006.01)
*A61B 1/005* (2006.01)

(52) U.S. Cl.
CPC ............ *A61B 1/00096* (2013.01); *A61B 1/04* (2013.01); *G02B 23/24* (2013.01)

(56) References Cited

U.S. PATENT DOCUMENTS

| | | | | |
|---|---|---|---|---|
| 4,779,613 A | * | 10/1988 | Hashiguchi | A61B 1/00179 359/512 |
| 5,438,975 A | * | 8/1995 | Miyagi | A61B 1/00071 600/109 |
| 7,322,934 B2 | * | 1/2008 | Miyake | A61B 1/05 600/114 |
| 8,228,369 B2 | | 7/2012 | Kojima et al. | |
| 9,313,382 B2 | * | 4/2016 | Igarashi | A61B 1/051 |
| 2006/0044450 A1 | * | 3/2006 | Wolterink | H01L 27/14627 348/340 |
| 2007/0052050 A1 | * | 3/2007 | Dierickx | H01L 27/14629 257/432 |
| 2007/0117254 A1 | * | 5/2007 | Pain | H01L 27/14621 438/75 |
| 2008/0300457 A1 | * | 12/2008 | Hosaka | A61B 1/12 600/110 |
| 2009/0171150 A1 | * | 7/2009 | Iede | A61B 1/018 600/112 |
| 2009/0171160 A1 | * | 7/2009 | Ito | A61B 1/0055 600/141 |
| 2009/0244259 A1 | * | 10/2009 | Kojima | H04N 5/2251 348/45 |
| 2010/0152540 A1 | * | 6/2010 | Tanoue | G02B 23/2469 600/175 |
| 2011/0226510 A1 | | 9/2011 | Sekido | |
| 2012/0008934 A1 | | 1/2012 | Kawasaki | |
| 2012/0029289 A1 | | 2/2012 | Kucklick | |
| 2013/0188030 A1 | * | 7/2013 | Igarashi | A61B 1/00064 348/65 |
| 2016/0066774 A1 | * | 3/2016 | Fujimori | H04N 5/2253 600/112 |
| 2016/0324403 A1 | * | 11/2016 | Yeoh | A61B 1/00165 |
| 2017/0165456 A1 | * | 6/2017 | Tutungi | A61M 25/0009 |
| 2018/0360352 A1 | * | 12/2018 | Ohno | A61B 5/1455 |
| 2019/0082944 A1 | * | 3/2019 | Fujimori | H04N 5/2251 |

FOREIGN PATENT DOCUMENTS

| | | |
|---|---|---|
| JP | S63-65840 A | 3/1988 |
| JP | 08-280603 A | 10/1996 |
| JP | 2001-128930 A | 5/2001 |
| JP | 2005-312555 A | 11/2005 |
| JP | 2009-240634 A | 10/2009 |
| JP | 2011-103931 A | 6/2011 |
| JP | 2012-018993 A | 1/2012 |
| JP | 2012-055570 A | 3/2012 |
| JP | 2012-075658 A | 4/2012 |
| JP | 2013-537446 A | 10/2013 |
| WO | WO 2012/032934 A1 | 3/2012 |

* cited by examiner

ENDOSCOPE

CROSS REFERENCE TO RELATED APPLICATION

This application is a continuation application of PCT/JP2016/081041 filed on Oct. 20, 2016 and claims benefit of PCT/JP2015/080181 filed on Oct. 27, 2015, the entire contents of which are incorporated herein by this reference.

BACKGROUND OF THE INVENTION

Field of the Invention

The present invention relates to an endoscope including an insertion portion that includes a distal end portion in which an image pickup module is disposed and a bending portion configured to change a direction of the distal end portion.

Description of the Related Art

For invasiveness reduction, endoscopes have increasingly been thinned. On the other hand, for insertion into an ultra-thin lumen, for example, a blood vessel or a small bronchus, an ultra-thin endoscope is needed. However, by only following the thinning technique for invasiveness reduction, it is not easy to provide an ultra-thin endoscope having a diameter of, for example, less than 1 mm.

Description of U.S. Patent Application Publication No. 2012/0008934 discloses an image pickup module including a wafer-level stack. The image pickup module is fabricated by bonding a lens wafer including a plurality of lenses and an image pickup wafer including a plurality of image pickup devices to each other and subsequently cutting the bonded wafers into individual pieces.

On the other hand, as disclosed in the description of U.S. Pat. No. 8,228,369, in an endoscope including an image pickup module disposed in a distal end portion of an insertion portion, a fixed end of an operation wire, which is a drive member for a bending portion, is fixed to the vicinity of a boundary between a rigid distal end portion and the bending portion, which is distant from the image pickup module.

In an ultra-thin endoscope, a wafer-level stack is an important component. Use of a wafer-level stack as an image pickup module enables thinning of a distal end portion of an endoscope. However, even though a wafer-level stack is used, if an operation wire is fixed at a position distant from the image pickup module as in conventional image pickup modules, the distal end portion becomes long.

Also, it is preferable that when the operation wire is operated, a direction in which the image pickup module performs shooting (view direction) move (upward/downward or leftward/rightward). However, in the case of an ultra-thin endoscope, it is not easy to fix an operation wire at a predetermined position relative to the image pickup module. If the operation wire is not fixed at a proper position, a view direction is moved obliquely by an operation of the operation wire and thus the operability is poor.

SUMMARY OF THE INVENTION

An endoscope according to an embodiment includes: an insertion portion that includes a distal end portion, and a bending portion configured to change a direction of the distal end portion, the bending portion being provided so as to extend from the distal end portion, and the distal end portion includes a casing having a round shape in a cross-section, and an image pickup module that includes an optical module section including a plurality of optical members and an image pickup section, the image pickup module having a rectangular shape in a cross-section, the image pickup section includes an image pickup device, and a semiconductor stack in which a plurality of semiconductor devices is stacked, and entirety of the image pickup module is completely housed inside the casing.

An endoscope according to another embodiment includes an insertion portion that includes a distal end portion, and a bending portion configured to change a direction of the distal end portion, the bending portion being provided so as to extend from the distal end portion, and the distal end portion includes a casing having a round shape in a cross-section, and an image pickup module that includes an optical module section including a plurality of optical members and an image pickup device, the image pickup module having a rectangular shape in a cross-section, an end portion of a drive member configured to bend the bending portion is a fixed end inserted and fixed in a space over a side face of the image pickup module, and a maximum length of a cross-section of the space is no less than 100% and no more than 112.5% of an outer dimension of the fixed end.

DETAILED DESCRIPTION OF THE PREFERRED EMBODIMENT(S)

First Embodiment

Figure 1:
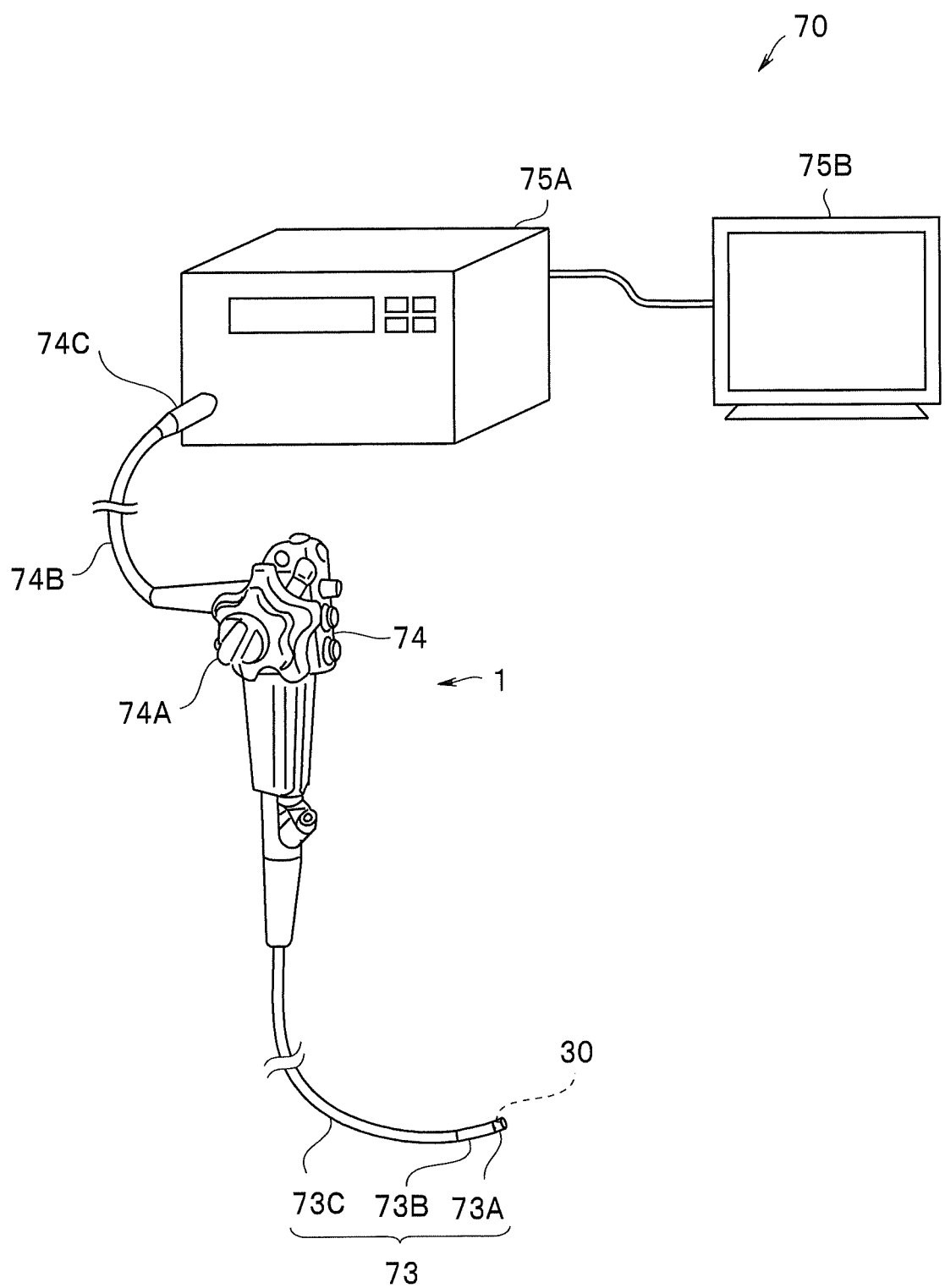
FIG. 1 is a perspective view of an endoscope system including an endoscope according to a first embodiment.

As illustrated in FIG. 1, an endoscope system 70 includes an endoscope 1 according to the present embodiment, a processor 75A and a monitor 75B. Insertion of an elongated insertion portion 73 into a body cavity of a subject allows the endoscope 1 to pick up an image of the inside of the subject and output an image pickup signal.

Note that in the following description, drawings based on the respective embodiments are schematic ones; and, e.g., a relationship between a thickness and a width of each part and ratios in thickness among, and relative angles between, the respective parts are different from actual ones, and parts that are different in dimensional relationship and/or ratio depending on the drawings may be included in the drawings. Also, illustration of some components may be omitted.

The endoscope 1 includes the insertion portion 73, a grasping portion 74 disposed on the proximal end portion side of the insertion portion 73, a universal cord 74B provided so as to extend from the grasping portion 74, and a connector 74C disposed on the proximal end portion side of the universal cord 74B. The insertion portion 73 includes a rigid distal end portion 73A in which an image pickup module 30 is disposed, a bendable bending portion 73B for changing a direction of the distal end portion 73A, the bendable bending portion 73B being provided on the proximal end side of the distal end portion 73A, and a flexible portion 73C provided so as to extend on the proximal end side of the bending portion 73B. The endoscope 1 is a flexible endoscope but may be a rigid endoscope if such an endoscope includes a bending portion. In other words, the flexible portion etc., are not critical components for an endoscope according to an embodiment.

A pivoting angle knob 74A, which is an operation portion for a surgeon to operate the bending portion 73B, is disposed at the grasping portion 74.

The universal cord 74B is connected to a processor 75A via the connector 74C. The processor 75A controls the entire endoscope system 70 and performs signal processing of an image pickup signal outputted by the image pickup module 30 and outputs the resulting image signal. A monitor 75B displays the image signal outputted by the processor 75A, in the form of an endoscopic image.

Figure 2:
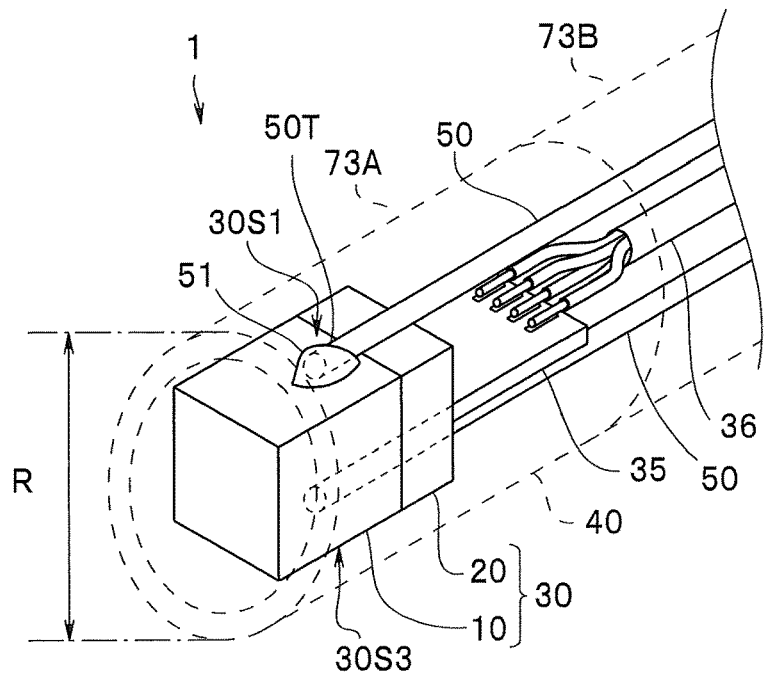
FIG. 2 is a perspective transparent view of a distal end portion of the endoscope according to the first embodiment.
Figure 3:
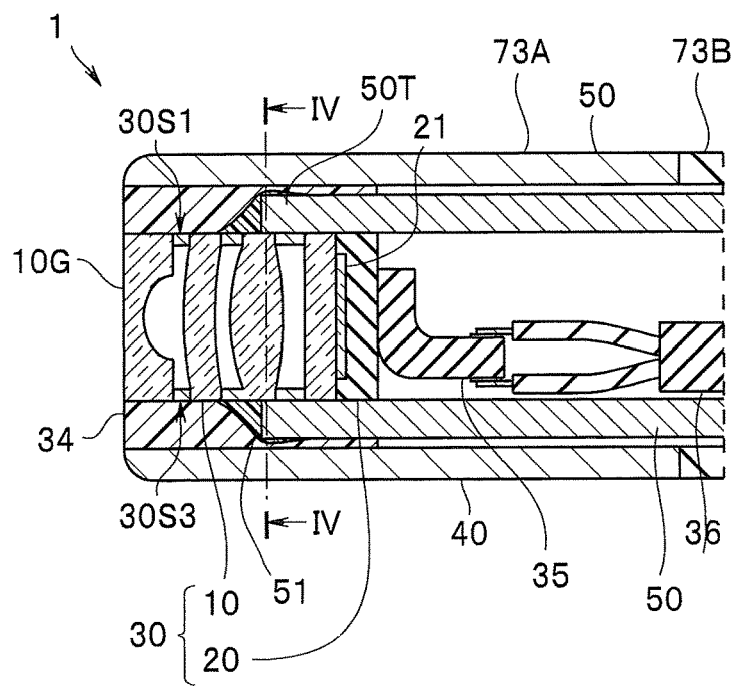
FIG. 3 is a cross-sectional view of the distal end portion of the endoscope according to the first embodiment.
Figure 4:
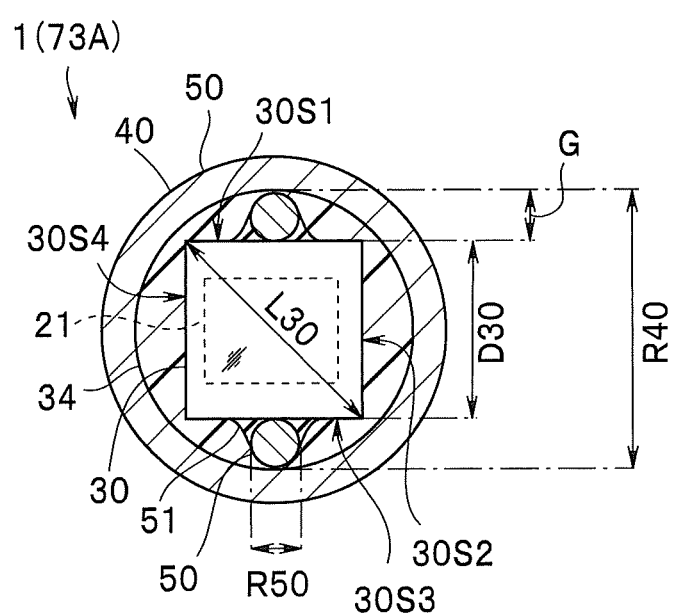
FIG. 4 is a cross-sectional view along line IV-IV of the endoscope according to the first embodiment in FIG. 3.

As illustrated in FIGS. 2 to 4, the distal end portion 73A of the endoscope 1 includes a casing 40 having a cylindrical shape (having a round shape in a cross-section in a direction orthogonal to an optical axis), the casing 40 housing the image pickup module 30 having a substantially cuboid shape (having a rectangular shape in a cross-section in the direction orthogonal to the optical axis) inside. A sealing resin 34 such as a silicone resin or an epoxy resin is charged inside the casing 40 including, for example, a metal such as a stainless steel, which is a rigid material. Here, an outer face of the casing 40 may be covered by a non-illustrated resin layer. Also, a corner of the distal end portion 73A is chambered.

It is desirable that the material of the casing 40 have a light shielding property. Use of a light shielding material as the material of the casing 40 can further prevent light entering from side faces of the image pickup module 30 from affecting a light receiving section 21.

In the image pickup module 30, an optical module section 10 and an image pickup device 20 are stacked in a layered form. A light receiving section 21 including, e.g., a CCD or CMOS image pickup device is formed in a light receiving surface of the image pickup device 20 including a semiconductor. Although not illustrated, a plurality of external electrodes electrically connected to the light receiving section 21 is disposed on a rear face of the image pickup device 20, the rear face opposite to the light receiving surface, via, e.g., a through-wiring. The plurality of external electrodes is electrically connected to a signal cable 36 via a wiring board 35.

Here, as illustrated in FIG. 4, the light receiving section 21 of the image pickup device 20 has a substantially rectangular shape. Then, the four sides of the light receiving section 21 are parallel to the four sides of a cross-section, in a direction orthogonal to an optical axis, of the image pickup module 30, respectively.

Then, fixed ends 50T that are opposite ends of an operation wire 50, which is a drive member configured to bend the bending portion 73B, are inserted in respective spaces between two opposite side faces 30S1, 30S3 of the image pickup module 30 and an inner face of the casing 40, over the substantial centers of the side faces 30S1, 30S3, and the respective fixed ends are fixed to the relevant side faces 30S1, 30S3 via an adhesive 51. The operation wire 50 is a metal wire having a round shape in a cross-section in a direction orthogonal to a longitudinal axis.

Here, for thinning the distal end portion 73A, it is preferable that an inner diameter R40 of the casing 40 be slightly larger than a length L30 of a diagonal line of the rectangle of the cross-section in the direction orthogonal to the optical axis of the cuboid image pickup module 30. For example, the relationship indicated by Expression 1 below is preferable, and the relationship indicated by Expression 2 is particularly preferable.

$$L30 \leq R40 \leq 1.25 \times L30 \quad \text{(Expression 1)}$$

$$L30 \leq R40 \leq 1.10 \times L30 \quad \text{(Expression 2)}$$

Furthermore, it is preferable that an outer diameter R50 of (each fixed end of) the operation wire 50, a length D30 of the cross-section in the direction orthogonal to the optical axis of the image pickup module 30 and the inner diameter R40 of the casing 40 be in the relationship indicated by Expression 3 below, and particularly preferably the relationship indicated by Expression 4.

$$(R50+D30+R50) \leq R40 \leq 1.25 \times (R50+D30+R50) \quad \text{(Expression 3)}$$

$$(R50+D30+R50) \leq R40 \leq 1.10 \times (R50+D30+R50) \quad \text{(Expression 4)}$$

In other words, a maximum length G of each of the spaces over the side faces of the image pickup module 30 in the cross-section in the direction orthogonal to the optical axis, in which the operation wire 50 is inserted, is no less than 100% and no more than 112.5% of the diameter (outer dimension) R50 of the operation wire 50.

In other words, $R50 \leq G \leq 1.125 \times R50$ (Expression 5) is preferable, and $R50 \leq G \leq 1.05 \times R50$ (Expression 6) is particularly preferable.

If the outer diameter of the operation wire 50 is out of the aforementioned range, the fixed ends are processed so as to cause the outer diameter of each fixed end to fall within the range. For example, the operation wire 50 is ground to decrease the outer diameter or a film of another member, for example, solder is formed on an outer face of the operation wire 50 to increase the outer diameter.

In the endoscope 1, the operation wire 50 is inserted in each of the respective spaces between the side faces 30S1, 30S3 of the image pickup module 30 and the inner face of the casing 40. Thus, an increase in diameter R of the casing 40 due to disposition of the operation wire 50 is prevented. In other words, the inner diameter of the casing 40 is selected so as to be slightly larger than a minimum diameter that enables insertion of the operation wire 50 having a diameter of, for example, 10 μm to 100 μm into the respective spaces. A thickness of the casing 40 is, for example, 50 μm to 100 μm.

Therefore, the diameter R40 of the casing 40 is, for example, no more than 2 mm and thus, is small. Also, an ultra-thin endoscope including a casing 40 having a diameter R40 of less than 1 mm, which is hard to provide by following the conventional techniques, can be provided.

Note that, for example, light guides configured to guide illuminating light may be inserted through respective spaces between side faces 30S2, 30S4 of the image pickup module 30 and the inner face of the casing 40, in which the operation wires 50 are not inserted. Also, the cross-sectional shape of the image pickup module 30 may be a rectangular shape having sides having different lengths.

Figure 5:
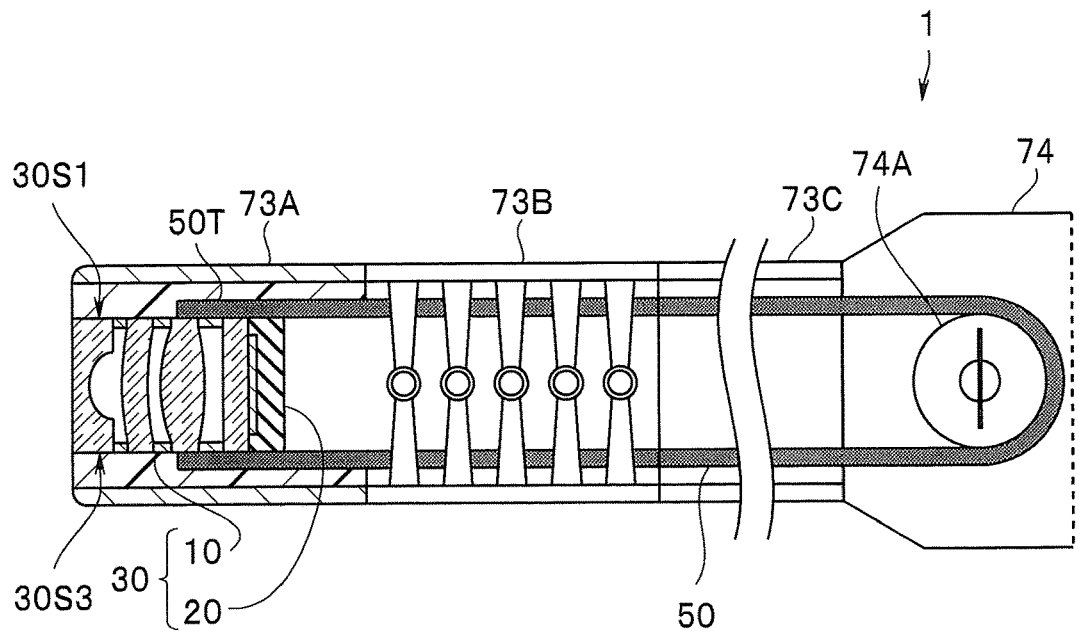
FIG. 5 is a schematic cross-sectional view for describing a bending operation of the endoscope according to the first embodiment.

Next, an operation for bending, which is performed via the angle knob 74A, will be described. As illustrated in FIG. 5, one end portion (first end portion) of the operation wires 50 is fixed to the side face 30S1, the other end portion (second end portion) of the operation wires 50 is fixed to the side face 30S3, and an intermediate portion of the operation wires 50 is fixed to the angle knob 74A.

Figure 6:
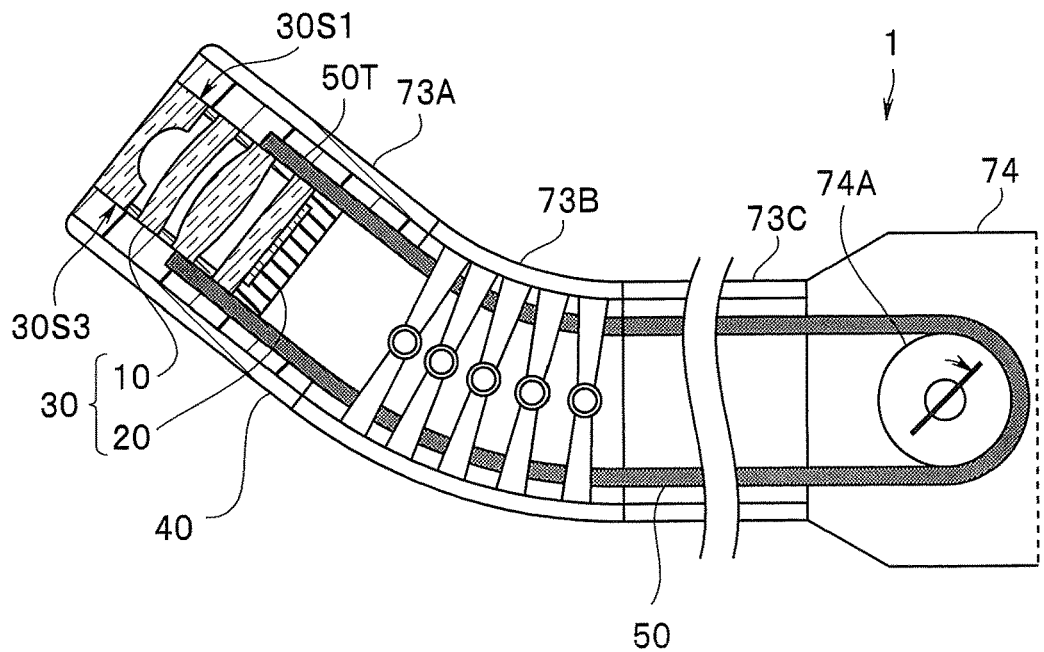
FIG. 6 is a schematic cross-sectional view for describing a bending operation of the endoscope according to the first embodiment.

As illustrated in FIG. 6, upon the angle knob 74A being operated so as to pivot, for example, clockwise by a surgeon, the part of the operation wire 50 fixed to the side face 30S1 is pulled, and on the other hand, the part of the operation wire 50 fixed to the side face 30S3 is pushed out. Thus, the bending portion 73B bends upward in the figure (toward the side face 30S1). Contrarily, upon the angle knob 74A being operated so as to pivot counterclockwise, the bending portion 73B bends downward.

Figure 7:
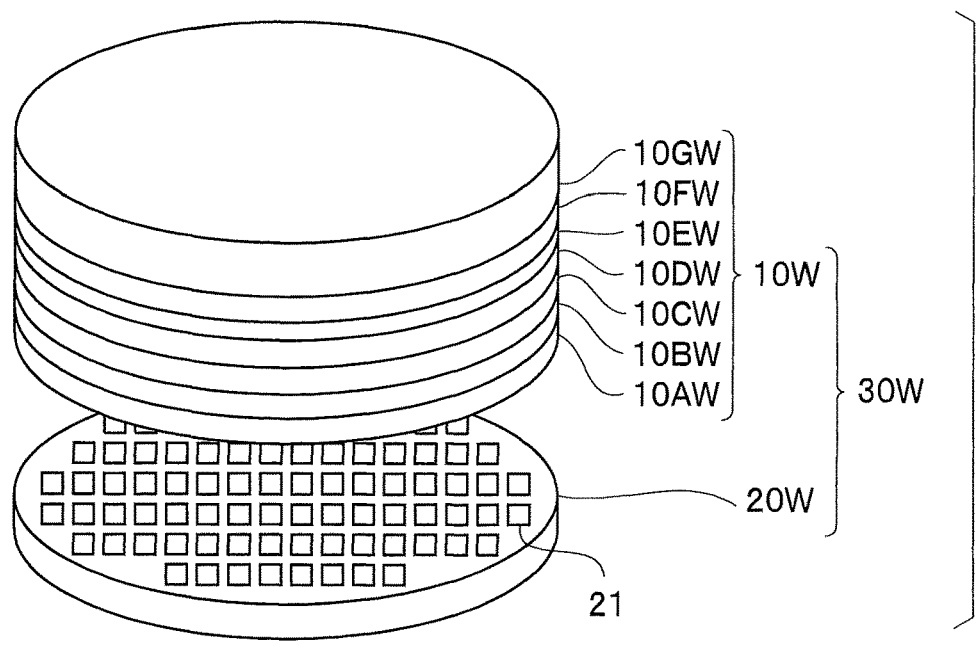
FIG. 7 is a diagram for describing a method for manufacturing an image pickup module in the endoscope according to the first embodiment.
Figure 8:
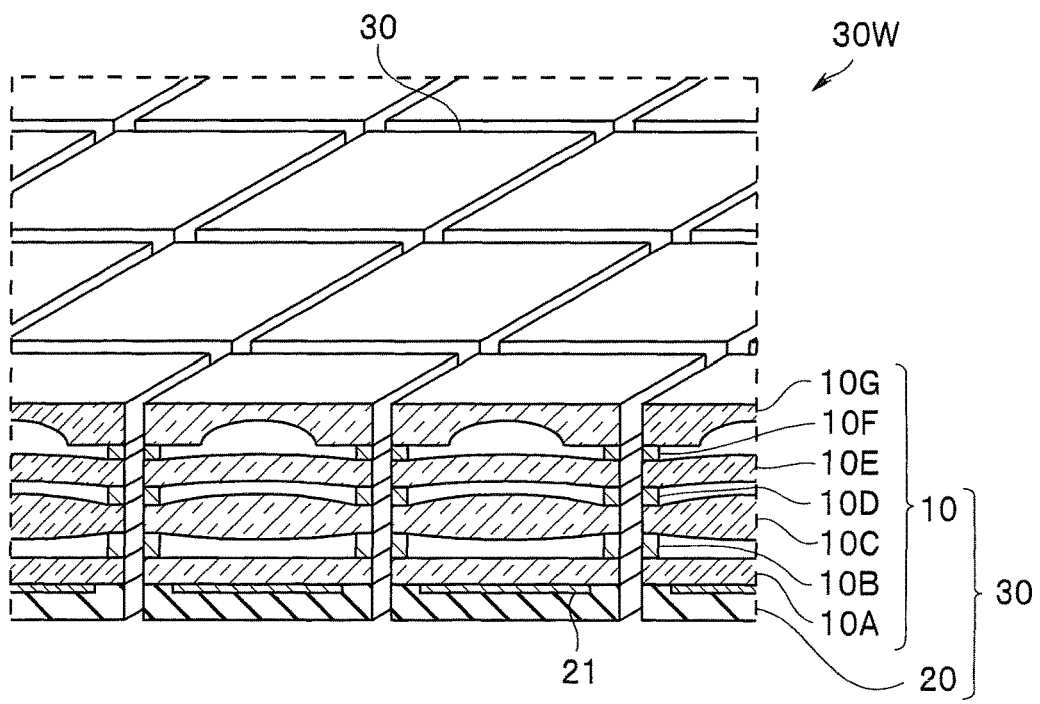
FIG. 8 is a diagram for describing a method for manufacturing the image pickup module in the endoscope according to the first embodiment.

Next, a method for manufacturing the image pickup module 30 will be described. As already described, in the image pickup module 30, the optical module section 10 and the image pickup device 20 are stacked in a layered form. As illustrated in FIGS. 7 and 8, the optical module section 10 is a stack in which a plurality of optical members 10A to 10G has been stacked in a layered form at wafer level.

In an image pickup wafer 20W, a plurality of light receiving sections 21 etc., is disposed on, e.g., a silicon wafer, using a publicly known semiconductor manufacturing technique. Peripheral circuits each configured to perform primary processing of output signals from the relevant light receiving section 21 or processing of drive control signals may be formed on the image pickup wafer 20W.

An optical member stacked wafer 10W is a stack of optical member wafers 10AW to 10GW each including a plurality of optical elements formed on the optical member wafer. For example, optical member wafers 10AW, 10CW, 10EW, 10GW are wafers each including a transparent member, and optical member wafers 10BW, 10DW, 10FE between the respective optical member wafers 10AW, 10CW, 10EW, 10GW are spacer wafers in which parts each serving as an optical path are through holes.

As illustrated in FIG. 8, the image pickup module 30 is a wafer-level stack fabricated by cutting a stacked wafer 30W in which the image pickup wafer 20W and the optical member stacked wafer 10W are stacked into individual pieces.

The respective wafers are joined via, for example, a transparent adhesive or are directly bonded. Note that the order of stacking of the wafers can be changed as necessary. For example, in order to protect the light receiving section 21 of the image pickup wafer 20W, an optical member wafer 10AW including a flat glass plate may be joined to the image pickup wafer 20W, and after disposition of external electrodes on a rear face, an optical member stacked wafer including the optical member wafers 10BW to 10GW may be stacked on the optical member wafer 10AW.

Also, the stacking may be performed after each of the image pickup wafer 20W and the optical member stacked wafer 10W being cut into individual pieces, rather than the stacked wafer 30W in which the image pickup wafer 20W and the optical member stacked wafer 10W are stacked being cut into individual pieces.

Then, the stacked wafer 30W is cut into individual image pickup modules 30, which are cuboid wafer-level stacks, in such a manner that the four sides of a substantially rectangular light receiving section 21 of each image pickup device 20 are parallel to the respective four sides of a rectangular cross-section orthogonal to an optical axis of the relevant image pickup module 30. Here, after the cutting, corner portions of the image pickup module 30, the corner portions being parallel to the optical axis, may be chamfered in such a manner that the image pickup module 30 has a polygonal shape in a cross-section in the direction orthogonal to the optical axis.

The individual image pickup modules 30 are housed inside respective cylindrical casings 40. As already described, the inner diameter R40 of each casing 40 is slightly larger than the length L30 of a diagonal line of the rectangle of the cross-section of the cuboid image pickup module 30.

Then, the outer diameter (outer dimension) R50 of the operation wire 50, which is a drive member, is substantially the same as the maximum length G of the cross-section in the direction orthogonal to the optical axis of each of the spaces in which the fixed ends of the image pickup module 30 are fixed. "Substantially the same" here means that the length G of the cross-section is slightly larger than the outer diameter R50 of the operation wire 50, which is clear from Expression 3 or Expression 4. Also, the maximum length G of the cross-section is a distance from a center point of a side face of the image pickup module 30 to a point at which a straight line vertically drawn from the center point of the side face meets the inner face of the casing 40.

Therefore, as illustrated in FIG. 4, upon insertion of the operation wire 50 into the spaces between the side faces of the image pickup module 30 and the inner face of the casing 40, distal end portions, that is, the fixed ends of the operation wire 50 are automatically disposed at the substantial centers of the side faces of the image pickup module 30 (image pickup device 20).

As a result of the adhesive 51 being applied to the side faces of the image pickup module 30 in advance, the fixed ends of the operation wire 50 are fixed to the side faces of the image pickup module 30. Furthermore, the sealing resin 34 is charged between the side faces of the image pickup module 30 and the inner face of the casing 40. The sealing resin 34 may double as the adhesive 51.

At the time of manufacture of the endoscope 1, the fixed ends of the operation wire 50 are automatically fixed at the substantial centers of the side faces of the image pickup module 30 (image pickup device 20). Therefore, in the endoscope 1, a direction of movement of the distal end portion 73A by an operation to bend the bending portion 73B is orthogonal to or parallel to an endoscopic image picked up by the light receiving section 21. In other words, an observation direction (view) moves upward/downward or leftward/rightward in an endoscopic image via an operation to bend the bending portion 73B, and thus, the endoscope 1 has good operability.

As described above, the endoscope 1 in which the operation wires 50 are fixed at the centers of the side faces of the small and substantially cuboid image pickup module 30 includes a thin distal end portion 73A and has good operability.

Note that, in the endoscope 1, the opposite ends of a single operation wire 50 are fixed to the two opposite side faces 30S1, 30S3 of the image pickup module 30. On the other hand, an endoscope according to another embodiment may include a single operation wire connecting one side face 30S1 of the image pickup module and an angle knob 74A alone. Note that an endoscope including such a single operation wire alone only allows an operation for bending in one direction. However, for example, other functional members can be inserted through respective spaces between three side faces of an image pickup module and a casing.

Also, one operation wire may connect the side face 30S1 and the angle knob 74A and another operation wire may connect the side face 30S3 and the angle knob 74A. In other words, instead of the operation wire 50, two operation wires having a same function may be used.

Also, fixed ends of an operation wire other than the operation wire 50 may be fixed to respective two side faces 30S2, 30S4 orthogonal to the side face 30S1 of the image pickup module 30 and the operation wire may be connected to an angle knob other than the angle knob 74A. For example, in an endoscope configured to be bent upward/downward via an angle knob 74A, a bending portion can be bent in a direction orthogonal to a direction of bending by pivoting the angle knob 74A, by pivoting another angle knob, that is, leftward/rightward.

Note that, in this case, an observation direction moves upward/downward and leftward/rightward in a picked-up image via operations for bending by the two angle knobs.

As described above, in an endoscope according to an embodiment, it is only necessary that a fixed end of an operation wire be fixed to at least one side face of an image pickup module 30.

Note that another functional member may further be inserted through either of the spaces between the side faces of the image pickup module 30 to which the operation wire 50 is fixed and the casing 40.

Also, an endoscope according to an embodiment may be a side viewing endoscope including an image pickup module in which an optical module includes a prism.

Here, in the endoscope 1, it is preferable that a strength of fixation of each of the fixed ends 50T of the operation wire 50, which is a drive member, to the image pickup module 30 be set to be equal to or lower than a predetermined strength.

As already described, the endoscope 1 is ultra-thin. Thus, the endoscope 1 can be inserted into a narrow lumen into which a conventional endoscope cannot be inserted. Since a narrow lumen has a small wall thickness, an endoscope is required to have higher safety.

In the endoscope according to the present embodiment, the strength of fixation of each of the fixed ends 50T of the operation wire 50 to the image pickup module 30 is set to be equal to or lower than a predetermined strength. Thus, if the bending portion 73B is largely bent by the operation wire 50 because of, e.g., an erroneous operation and the distal end portion 73A is strongly pressed against a wall surface of a lumen, the relevant fixed end 50T of the operation wire 50 comes off because of a repulsion force from the wall surface, and thus, the endoscope according to the present embodiment is highly safe.

The strength of fixation of the operation wire 50 is, for example, 1 kg, and the fixed ends 50T come off upon application of tensile stress that is equal to or higher than the strength.

If the fixed ends 50T of the operation wire 50 come off, an operation for bending cannot be performed, but a subject is prevented from being damaged. In particular, the ultra-thin endoscope 1 in which the outer diameter of the casing of the distal end portion is less than 1 mm is inserted into even a thin lumen having an inner diameter of less than 1 mm, that is, a lumen having a small wall thickness, and thus, particularly preferably has a fail-safe function.

Also, an operation wire having good conductivity may be used to provide the operation wire with a part of a function of the signal cable 36. For example, an operation wire obtained by forming a copper plating film on an outer periphery of the stainless steel wire may be bonded and fixed to electrodes on the side faces of the image pickup module 30 to use the operation wire as a ground potential wire or a signal wire for supplying a drive power signal. An endoscope including an operation wire having a signal wire function is thinner.

As described above, in an endoscope according to an embodiment, a distal end portion 73A includes a casing 40 having a round shape in a cross-section orthogonal to an optical axis, and an image pickup module 30 that includes an optical module section 10 including a plurality of optical members, and an image pickup device 20, the image pickup module 30 having a rectangular shape in a cross-section in the direction orthogonal to the optical axis. An end portion of an operation wire 50, which is a drive member configured to bend a bending portion 73B, is a fixed end inserted and fixed in a space over a side face of the image pickup module 30, and a maximum length G of a cross-section in the direction orthogonal to the optical axis of the space is no less than 100% and no more than 112.5% of an outer dimension of the fixed end of the operation wire 50.

Second Embodiment

Next, an endoscope 1A according to a second embodiment will be described. The endoscope 1A is similar to the endoscope 1 and has effects that are the same as effects of the endoscope 1, and thus, components having a same function are provided with same reference numerals and description of the relevant component is omitted.

Figure 9:
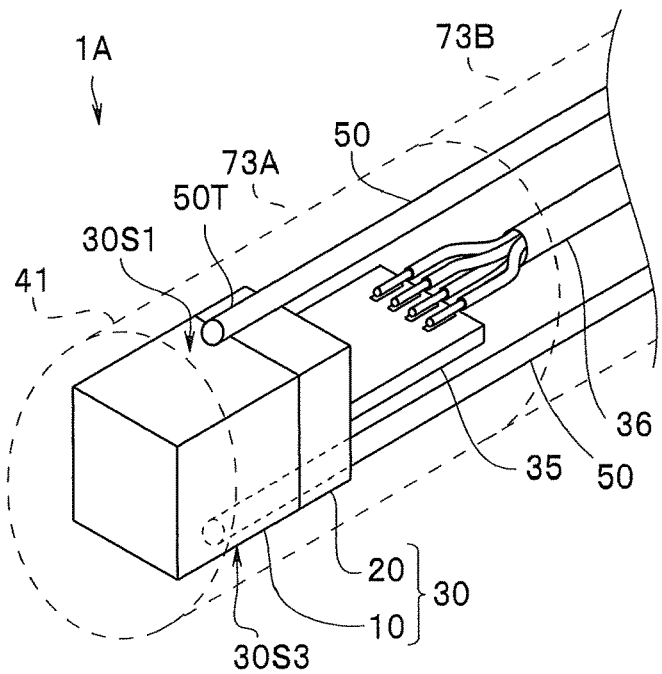
FIG. 9 is a perspective transparent view of a distal end portion of an endoscope according to a second embodiment.
Figure 10:
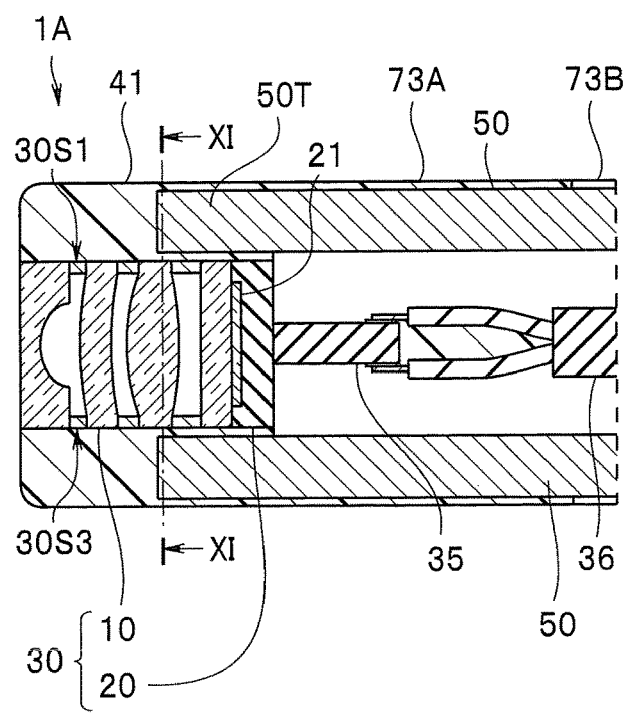
FIG. 10 is a cross-sectional view of the distal end portion of the endoscope according to the second embodiment.
Figure 11:
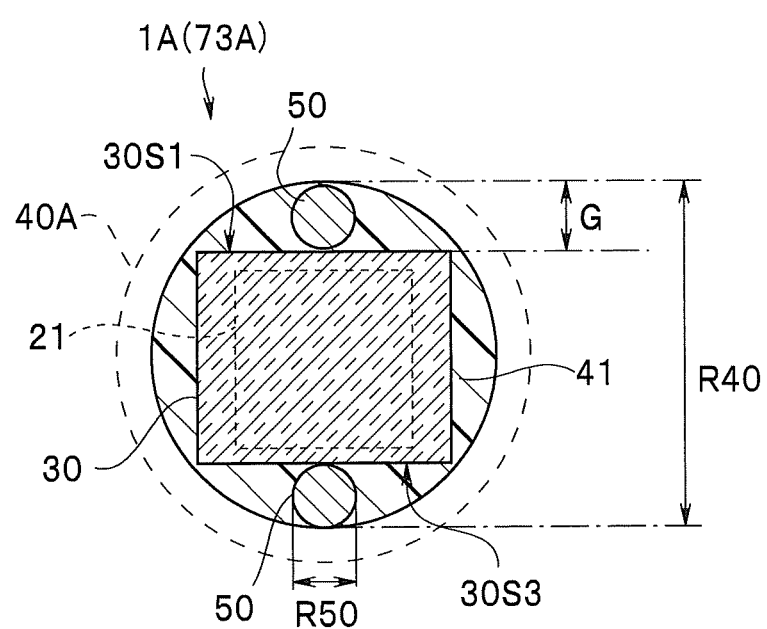
FIG. 11 is a cross-sectional view of the endoscope according to the second embodiment along line XI-XI in FIG. 10.

As illustrated in FIGS. 9, 10 and 11, in the endoscope 1A, a casing 41 includes a mold resin having a columnar shape (round shape in a cross-section in a direction orthogonal to an optical axis) in which an image pickup module 30 (having a rectangular shape in a cross-section in the direction orthogonal to the optical axis) is embedded. Then, fixed ends 50T of an operation wire 50 (having a round shape in a cross-section in the direction orthogonal to the optical axis), which is a drive member, are embedded in respective parts, over side faces 30S1, 30S2 of the image pickup module 30, of the casing 41.

In other words, in the endoscope 1A, also, the operation wire 50 is inserted and fixed in spaces between the side faces of the image pickup module 30 having a rectangular shape in a cross-section and an outer face of the casing 41 having a round shape in a cross-section.

For the casing 41, the image pickup module 30 is inserted into a mold 40A having a shape corresponding to the casing 41. Next, the operation wire 50 is inserted into respective spaces between the relevant side faces of the image pickup module 30 and the mold 40A. Then, a mold resin is injected into the spaces and subjected to cure treatment, and the casing 41 is thus fabricated. The mold resin is, e.g., an epoxy resin or a fluorine resin, which is a hard resin having a Rockwell hardness (JIS K7202-2, measurement temperature: 23° C.) of no less than HR100 on the R scale.

As with the inner diameter of the casing 40 of the endoscope 1, in an inner diameter of the mold 40A, a length of each of the spaces between an inner face of the mold 40A and the operation wire 50 is set. In other words, it is preferable that the inner diameter of the mold 40A meet, e.g., conditions obtained by replacement of the inner diameter R40 of the casing 40 in Expression 1 to Expression 6 with the inner diameter of the mold 40A.

If the above conditions are met, upon the operation wire 50 being disposed in the respective spaces between parts of the mold 40A on the relevant side faces of the image pickup module 30 and the side faces, the operation wire 50 is automatically disposed at substantial centers of the side faces.

The endoscope 1A is thinner than the endoscope 1 including a tubular body for holding, e.g., the image pickup module 30 in the distal end portion 73A. Also, the image pickup module 30 having a stacked structure is housed inside the mold resin including a member that is harder than the bending portion. Even if bending stress is applied to the distal end portion 73A as a result of an operation of the operation wire 50, the casing 41 including a hard mold resin does not deform. Thus, the image pickup module 30 having a stacked structure is protected from effects caused by operation of the operation wire 50.

Note that, in order to firmly fix the operation wire 50, the front side of the casing 41 may include a hard resin and the rear side of the casing 41 may include another soft resin.

Also, a light receiving section 21 can be prevented from being affected by light entering from side faces of the image pickup module 30 by covering the image pickup module 30 using a mold resin in which a light-shielding member such as carbon power is mixed. In this case, the covering of the image pickup module 30 extending to a rear face of the image pickup device 20 is particularly preferable because light penetrating silicon such as infrared light can be blocked.

Third Embodiment

Next, an endoscope 1B according to a third embodiment will be described. The endoscope 1B is similar to the endoscope 1 and has effects that are the same as the effects of the endoscope 1, and thus, components having a same function are provided with same reference numerals and description of the relevant component is omitted.

Figure 12:
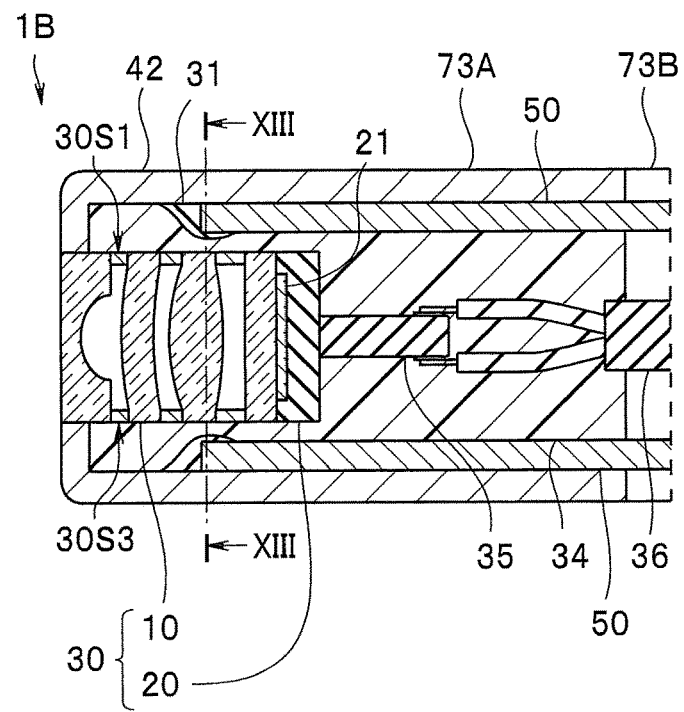
FIG. 12 is a cross-sectional view of a distal end portion of an endoscope of a third embodiment.
Figure 13:
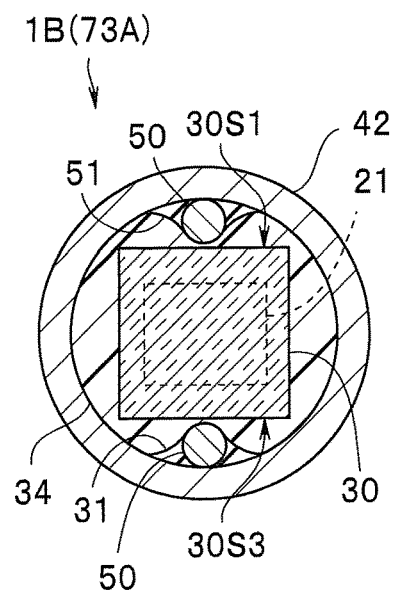
FIG. 13 is a cross-sectional view of the endoscope according to the third embodiment along line XIII-XIII in FIG. 12.

As illustrated in FIGS. 12 and 13, in the endoscope 1B, fixed ends 50T that are opposite ends of an operation wire 50, which is a drive member, are fixed to an inner face of a cylindrical casing 42 that houses an image pickup module 30 inside, respectively, via an adhesive 31. Positions at which the fixed ends 50T are fixed are located in respective areas over substantial centers of side faces 30S1, 30S3 of the image pickup module 30.

In other words, in the endoscope 1B, also, the operation wire 50 is inserted and fixed in the respective spaces between the side faces of the rectangular image pickup module 30 and the inner face of the casing 42.

The image pickup module 30 may be inserted after fixation of the fixed ends 50T of the operation wire 50 at two opposite positions in the inner face of the casing 42, or the operation wire 50 may be fixed to the casing 42 in which the image pickup module 30 is inserted.

As with the inner diameter of the casing 40 in the endoscope 1, it is preferable that an inner diameter of the casing 42 meet, e.g., the conditions of Expression 1 to Expression 6.

If the casing 42 meets the above conditions, the operation wire 50 is automatically disposed at substantial centers of the side faces of the image pickup module 30.

In the side faces of the image pickup module 30, e.g., glass, which is largely different in thermal expansion coefficient from the operation wire 50 including a metal and is subject to breakage is exposed. Thus, in the case of the endoscope 1, fixation of the operation wire 50 to the image pickup module 30 may be not easy. On the other hand, in the case of the endoscope 1B, the operation wire 50 is fixed to the inner face of the casing 42 including a metal, and thus, is easy to manufacture and has high reliability. Note that the fixation of the operation wire 50 to the inner face of the casing is not limited to fixation using an adhesive but may be fixation using solder bonding.

Note that the fixed ends of the operation wire 50 may be fixed to both the side faces of the image pickup module 30 and the inner face of the casing 42.

As described above, an endoscope in which an operation wire 50 is inserted and fixed in a space between a side face of a cuboid image pickup module 30, which is a wafer-level stack, and a casing having a round shape in a cross-section can easily be thinned, and have good operability because an observation direction is moved upward/downward (leftward/rightward) in an endoscopic image by an operation for bending.

Fourth Embodiment

Next, an endoscope 1C according to a fourth embodiment will be described. The endoscope 1C is similar to the endoscopes 1, 1A and 1B (hereinafter referred to as "endoscope 1 and the like") and has effects that are the same as the effects of the endoscope 1 and the like, and thus components having a same function are provided with same reference numerals and description of the relevant component is omitted.

Figure 14:
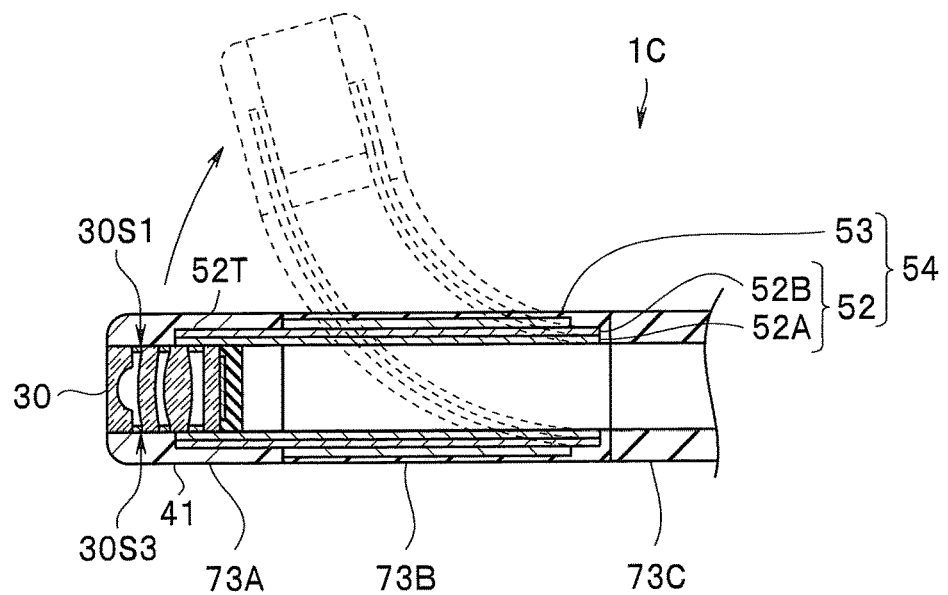
FIG. 14 is a schematic cross-sectional view for describing a bending operation of an endoscope according to a fourth embodiment.

As illustrated in FIG. 14, in the endoscope 1C, drive members for bending a bending portion 73B are bimetallic strips 52 on which a heater 53, which is a heating section, is disposed.

In each bimetallic strip 52, a first metal 52A and a second metal 52B that are different from each other in thermal expansion coefficient are stacked. Then, if the bimetallic strip 52 is heated by the relevant heater 53, the bimetallic strip 52 bends according to temperature variation resulting from the heating. Note that, although not illustrated, a conductive wire configured to supply power is connected to the heater 53, and is inserted through an insertion portion 73, and power supplied to the heater 53 is increased/decreased by pivoting an angle knob 74A of a grasping portion 74. Also, instead of the heater 53, the bimetallic strip 52 itself may be used as a heating element.

Respective end portions (fixed ends) 52T of two bimetallic strips 52 are fixed to respective side faces 30S1, 30S3 of an image pickup module 30.

Note that the fixed end 52T may be fixed to an area over the side face 30S1 of the image pickup module 30. In other words, as with the endoscope 1A, the fixed end 52T may be embedded in a casing 41 including a mold resin, or as with the endoscope 1B, the fixed end 52T may be fixed to an inner face of a cylindrical casing.

Figure 15:
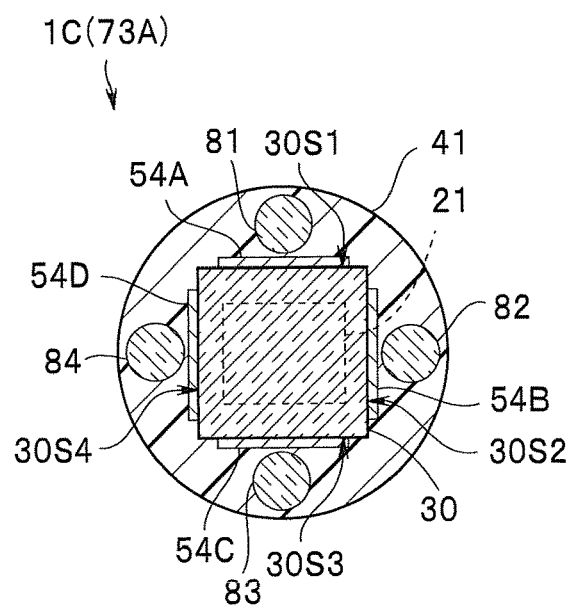
FIG. 15 is a cross-sectional view of a distal end portion of the endoscope according to the fourth embodiment.

As illustrated in FIG. 15, in the endoscope 1C, a columnar casing 41 includes a mold resin. Fixation portions of distal ends of respective drive members 54A to 54D are joined to areas over side faces 30S1 to 30S4 of the image pickup module 30 via an adhesive (not illustrated). Furthermore, four light guides 81 to 84 configured to guide illuminating light and an illumination optical system (not illustrated) are embedded in areas over the side faces 30S1 to 30S4 of the image pickup module 30.

Here, a direction of bending of each bimetallic strip 52 is different between a time when the bimetallic strip 52 is heated and a time when the bimetallic strip 52 is cooled. Therefore, a cooling section such as a Peltier device may be provided instead of the heater 53, which is a heating section. Also, disposing a heating section and a cooling section on one bimetallic strip 52 enables bending in two directions via the bimetallic strip 52.

The endoscope 1C includes no operation wire inserted through a flexible portion 73C, and thus has a simple structure and is thinner than the endoscope 1 etc.

Here, each of the drive members may be a bimorph piezoelectric body in which two piezoelectric bodies that are different from each other in a rate of deformation according to an applied voltage are stacked. In this case, instead of the heater 53, an electrode configured to apply a voltage is disposed on the bimorph piezoelectric body.

Since the bimorph piezoelectric bodies are higher in deformation speed than the bimetallic strips 52, and thus, have high responsiveness to an operation of an operation portion compared to the bimetallic strips 52.

As described above, the drive member is not limited to the operation wire 50 and may be, e.g., a bimetallic strip or a bimorph piezoelectric body if the bimetallic strip or the bimorph piezoelectric body can bend the bending portion.

Fifth Embodiment

Next, an endoscope 1D according to a fifth embodiment will be described. The endoscope 1D is similar to the endoscope 1 and the like and has effects that are the same as the effects of the endoscope 1 and the like, and thus, components having a same function are provided with same reference numerals and description of the relevant component is omitted.

Figure 16:
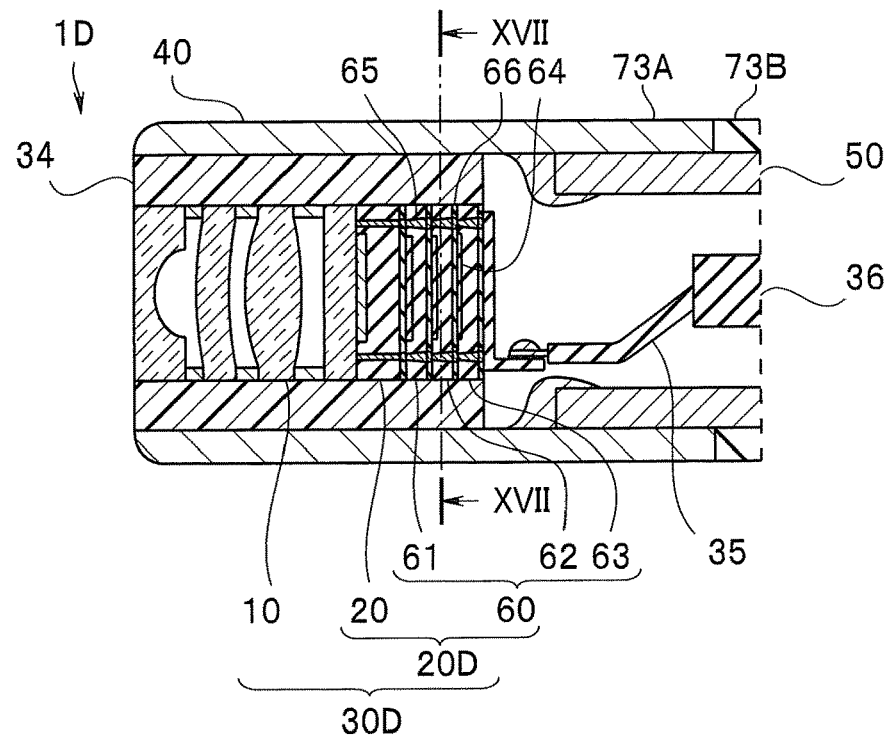
FIG. 16 is a cross-sectional view of a distal end portion of an endoscope according to a fifth embodiment.
Figure 17:
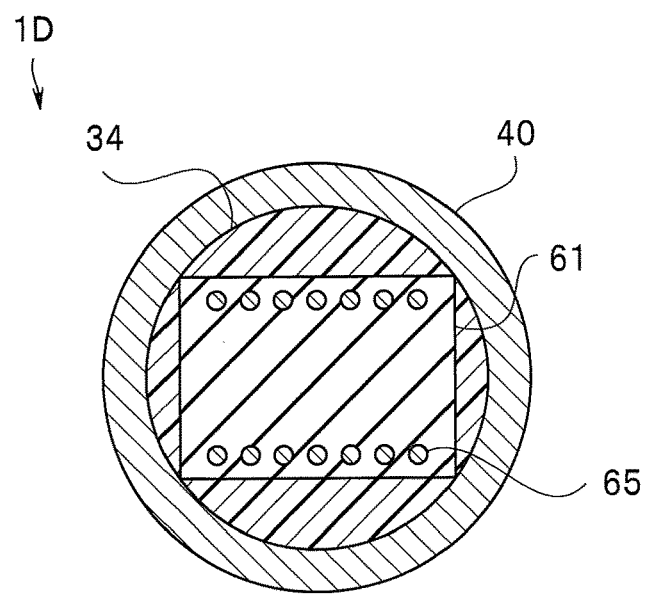
FIG. 17 is a cross-sectional view of the endoscope according to the fifth embodiment along line XVII-XVII in FIG. 16.

As illustrated in FIGS. 16 and 17, the endoscope 1D includes an insertion portion 73 that includes an distal end portion 73A and a bending portion 73B configured to change a direction of the distal end portion 73A, the bending portion 73B being provided so as to extend from the distal end portion 73A, and the distal end portion 73A includes a casing 40 having a round shape in a cross-section in a direction orthogonal to an optical axis, and an image pickup module 30D that includes an optical module section 10 including a plurality of optical members 10A to 10F, and an image pickup section 20D, the image pickup module 30D having a rectangular shape in a cross-section in the direction, and the image pickup section 20D includes an image pickup device 20 and a semiconductor stack 60 in which a plurality of semiconductor devices 61, 62, 63 is stacked, and entirety of the image pickup module 30D is completely housed inside the casing 40.

In the semiconductor stack 60, the plurality of semiconductor devices 61 to 63 is stacked via respective sealing resin layers 66. The semiconductor devices 61 to 63 in which a planer device 64 is formed are connected via respective through-wirings 65.

Entirety of the image pickup module 30D is completely housed inside the casing 40 having a round shape in a cross-section in the direction orthogonal to the optical axis. A signal cable 36 bonded to the stack 60 is provided to extend in a rear portion of the casing 40.

The semiconductor devices 61 to 63 in which a planer device 64 is formed each process an image signal generated by the image pickup device 20 and output the resulting signal to the signal cable 36. Each of the planer devices 64 is, e.g., a buffer, a capacitor, an inductor, a resistor, a denoising circuit or an analog-digital conversion circuit, and is one formed by what is called a semiconductor manufacturing process.

Figure 18:
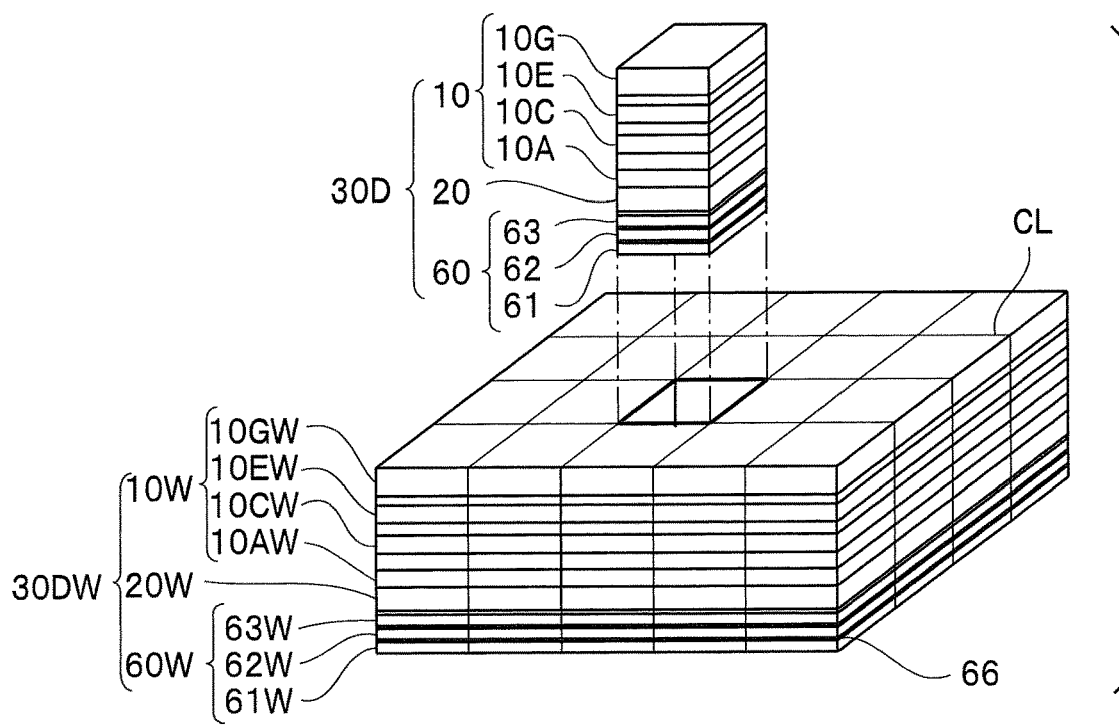
FIG. 18 is a perspective view of a stacked wafer for describing a method for manufacturing the endoscope according to the fifth embodiment.

As illustrated in FIG. 18, the image pickup module 30D is a wafer-level stack fabricated by cutting a stacked wafer 30DW. In the stacked wafer 30DW, an optical member stacked wafer 10W, an image pickup wafer 20W and a semiconductor stacked wafer 60W are stacked. In the optical member stacked wafer 10W, optical member wafers 10AW, 10CW, 10EW, 10GW are stacked. In the semiconductor stacked wafer 60W, semiconductor wafers 61W, 62W, 63W are stacked.

The semiconductor wafers 61W, 62W, 63W include pluralities of semiconductor devices 61, 62, 63, respectively. The pluralities of semiconductor devices 61, 62, 63 are the same in disposition in the respective semiconductor wafers 61W, 62W, 63W.

The image pickup module 30D in which the semiconductor stack 60 is bonded to a rear face of the image pickup device 20 is short. Furthermore, respective through vias 54 are formed in the semiconductor devices 61 to 63, and a size of projection on a surface orthogonal to the optical axis direction of the image stack 60 is a size that falls within a projection surface in the optical axis direction of the image pickup device 20.

The endoscope 1D includes the short and small-diameter image pickup module 30D and the distal end portion 73A is short and has a small diameter, and thus the endoscope 1D is less invasive.

Furthermore, the endoscope 1D is highly reliable because entirety of the image pickup module 30D is completely housed in the casing 40 that does not deform.

Figure 19A:
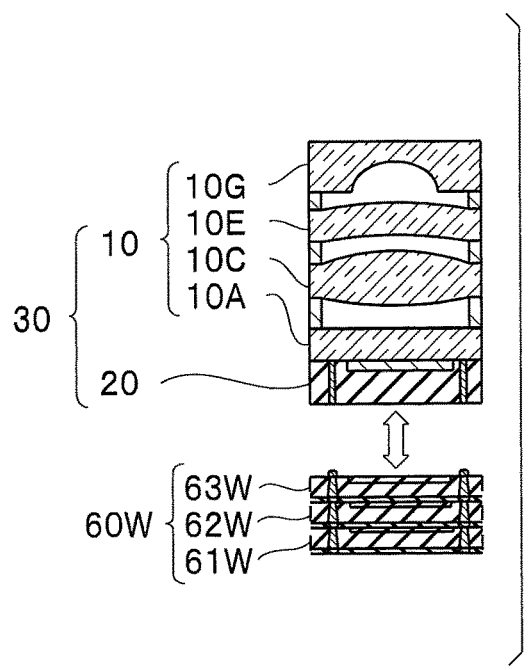
FIG. 19A is an exploded cross-sectional view for describing another method for manufacturing the endoscope according to the fifth embodiment.
Figure 19B:
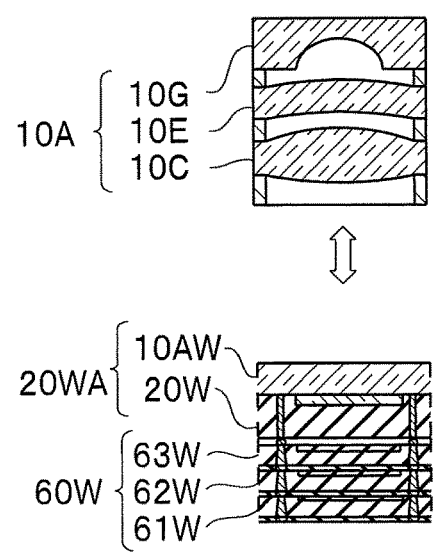
FIG. 19B is an exploded cross-sectional view for describing another method for manufacturing the endoscope according to the fifth embodiment.

Note that, in the endoscope 1D, the image pickup module 30D is a single wafer-level stack. On the other hand, as illustrated in FIG. 19A, a semiconductor stacked wafer 60W may be cut after disposition of an image pickup module 30, which is a wafer-level stack of an optical module section 10 and an image pickup device 20, on the semiconductor stacked wafer 60W. Also, as illustrated in FIG. 19B, an optical module section 10 may be joined to a stacked wafer of an image pickup wafer 20AW including a cover glass wafer 10AW and a semiconductor stacked wafer 60W.

Modification of Fifth Embodiment

Next, an endoscope 1E according to a modification of the fifth embodiment will be described. The endoscope 1E relates to the endoscopes 1 and 1A to 1D. The endoscope 1E is similar to the endoscopes 1 and 1A to 1D and has effects that are the same as the effects of the endoscopes 1 and 1A to 1D, and thus, components having a same function are provided with same reference numerals and description of the relevant component is omitted.

Figure 20:
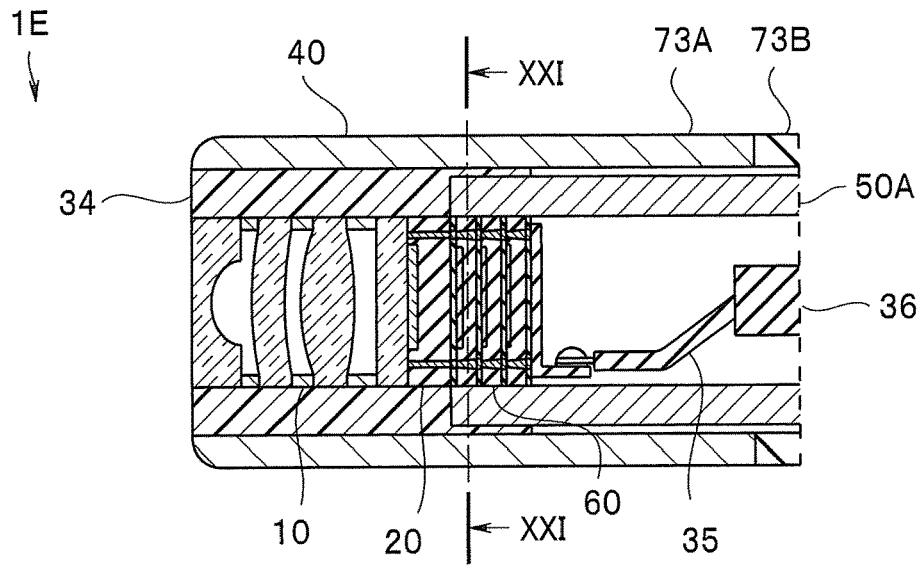
FIG. 20 is a cross-sectional view of a distal end portion of an endoscope according to a modification of the fifth embodiment.
Figure 21:
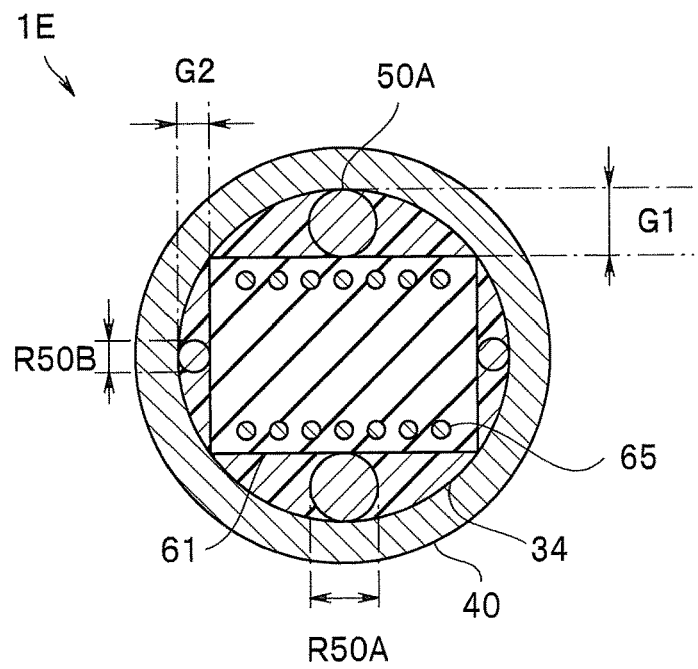
FIG. 21 is a cross-sectional view of the endoscope according to the modification of the fifth embodiment along line XXI-XXI in FIG. 20.

As illustrated in FIGS. 20 and 21, in the endoscope 1E, in addition to the configuration of the endoscope 1D, end portions of operation wires 50A, 50B are inserted and fixed in spaces over side faces of the image pickup module 30D.

A casing 40 has a cylindrical shape, and an image pickup module 30D has a rectangular shape in a cross-section. Thus, a maximum length of a cross-section of the space between a side face of the image pickup module 30D and an inner face of the casing 40 varies depending on the orthogonal side face of the image pickup module 30D.

In other words, where G1 is a maximum length of the space over a long-side side face, a maximum length G2 of the space over a short-side side face is smaller than G1.

It is preferable that the lengths G1, G2 of the spaces in which the operation wires 50A, 50B are inserted be no less than 100% and no more than 112.5% of respective outer diameters (outer dimensions) of the operation wires 50A, 50B. Therefore, the outer diameter R50B of the operation wire 50B is smaller than the outer diameter R50A of the operation wire 50A.

In the endoscope 1E, also, it should be understood that: the number of operation wires is not limited to four; and the endoscope 1E has the effects of both the endoscope 1 and the endoscope 1D even if the number of operation wires is two or one.

Sixth Embodiment

Next, an endoscope 1F according to a sixth embodiment will be described. The endoscope 1F is similar to the endoscope 1D and the like, and has effects that are the same as the effects of the endoscopes endoscope 1D and the like, and thus, components having a same function are provided with same reference numerals and description of the relevant component is omitted.

Figure 22:
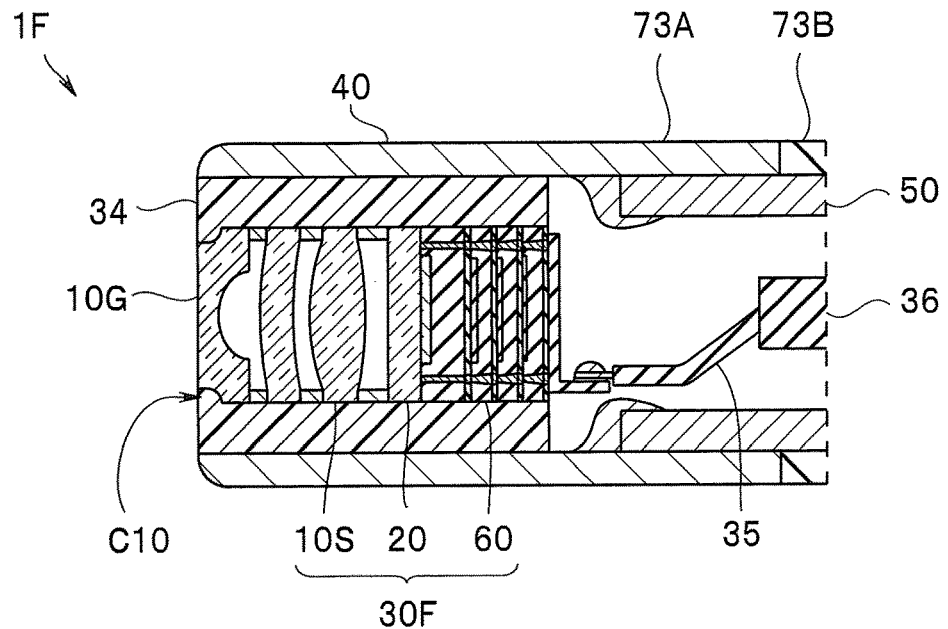
FIG. 22 is a cross-sectional view of a distal end portion of an endoscope according to a sixth embodiment.
Figure 23:
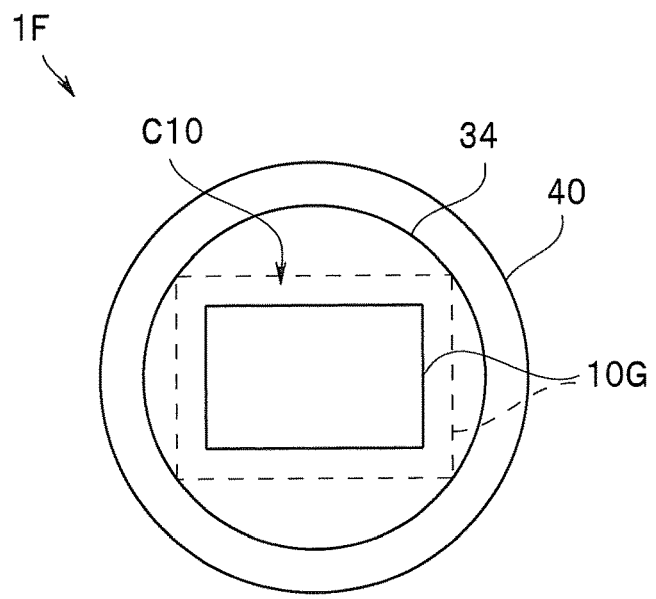
FIG. 23 is a front view of the distal end portion of the endoscope according to the sixth embodiment.

As illustrated in FIGS. 22 and 23, in the endoscope 1F, a stepped portion C10 is provided in an outer peripheral portion of a frontmost optical member 10G in an optical module section 10S, a sealing resin 34 covering an outer peripheral face of the optical module section 10S is charged in the stepped portion C10.

Figure 24:
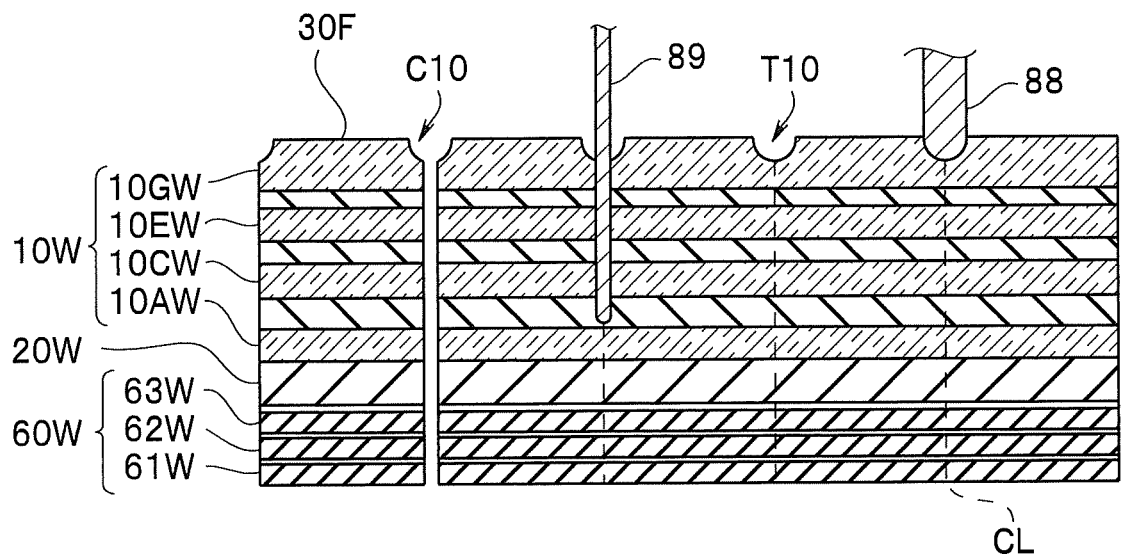
FIG. 24 is a cross-sectional view of a stacked wafer for describing a method for manufacturing the endoscope according to the sixth embodiment.

As illustrated in FIG. 24, two-step dicing (stepwise dicing) is performed in a step of cutting a stacked wafer 30DW in a process of manufacturing the endoscope 1E. For example, first, trenches T10 are formed along cutting lines CL in a most upper optical member wafer 10GW by a first dicing blade 88. Subsequently, the stacked wafer 30DW is cut into individual optical module sections 10S by a second dicing blade 89 having a width that is smaller than a width of the first dicing blade 88.

The optical module section 10S of the endoscope 1F is prevented from projecting from a front face of the casing 40, by the sealing resin 34 charged in the stepped portion C10.

Figure 25:
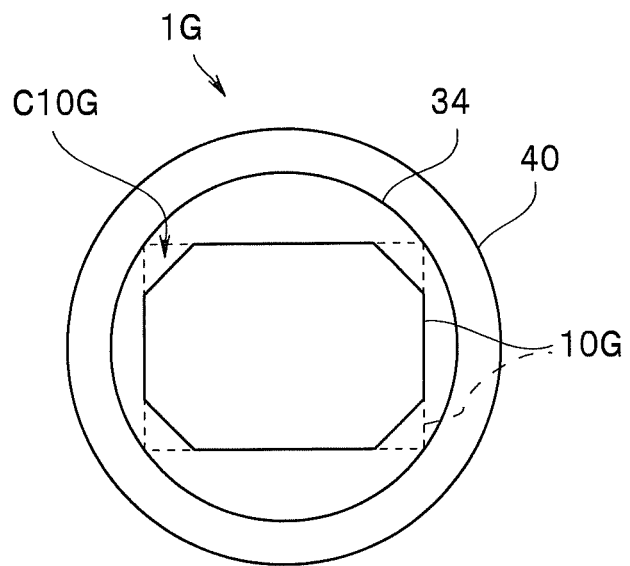
FIG. 25 is a front view of a distal end portion of an endoscope according to a modification of the sixth embodiment.

Note that, in the endoscope 1F, the stepped portion C10 is provided around the entire outer peripheral portion of the frontmost optical member 10G. However, like the endoscope 1G illustrated in FIG. 25, even if a stepped portion C10G is provided only in some parts, for example, corner portions of the outer peripheral portion of the optical member 10G, the endoscope 1G has effects that are the same as the effects of the endoscope 1F.

Seventh Embodiment and Eighth Embodiment

Next, an endoscope 1H according to a seventh embodiment and an endoscope 1I according to an eighth embodiment will be described. The endoscope 1H is similar to the endoscopes 1, 1D and 1F and the like, and has effects that are the same as the effects of the endoscope 1 and the like. Also, the endoscope 1I is similar to the endoscopes 1A, 1D and 1F and the like, and has effects that are the same as the effects of the endoscope 1 and the like. Thus, components having a same function are provided with same reference numerals and description of the relevant component is omitted.

Seventh Embodiment

Figure 26:
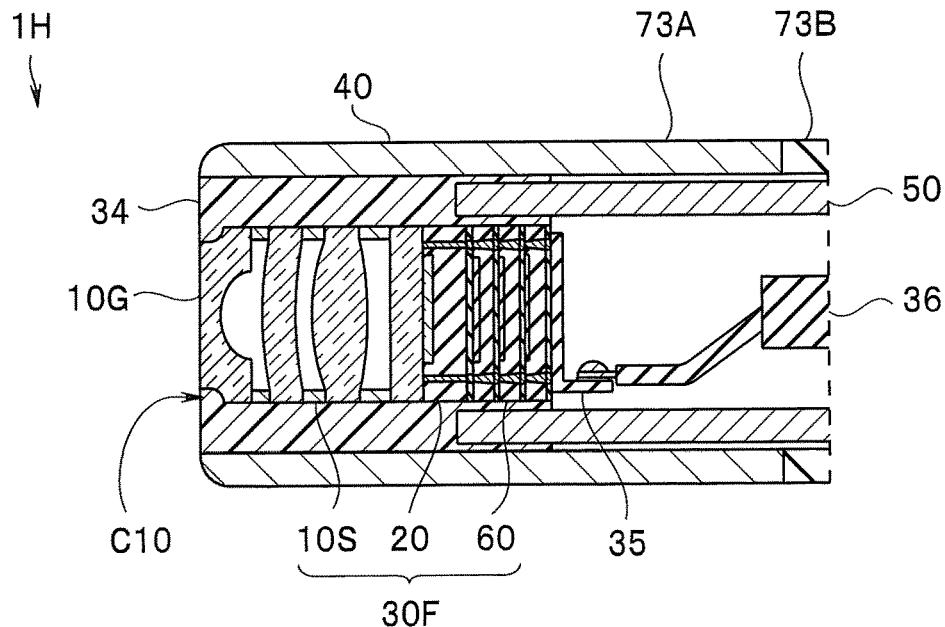
FIG. 26 is a cross-sectional view of a distal end portion of an endoscope according to a seventh embodiment.

As illustrated in FIG. 26, in the endoscope 1H, entirety of an image pickup module 30F is completely housed inside a cylindrical casing 40. Then, a maximum length G of a cross-section of each of spaces over side faces of the image pickup module 30F, in which end portions of an operation wire 50, which is a drive member, are fixed, is no less than 100% and no more than 112.5% of an outer dimension of the fixed end. Furthermore, a stepped portion C10 is provided in an outer peripheral portion of a frontmost optical member 10G in an optical module section 10S, and a sealing resin 34 covering an outer peripheral face of the optical module section 10S is charged in the stepped portion C10.

Eighth Embodiment

Figure 27:
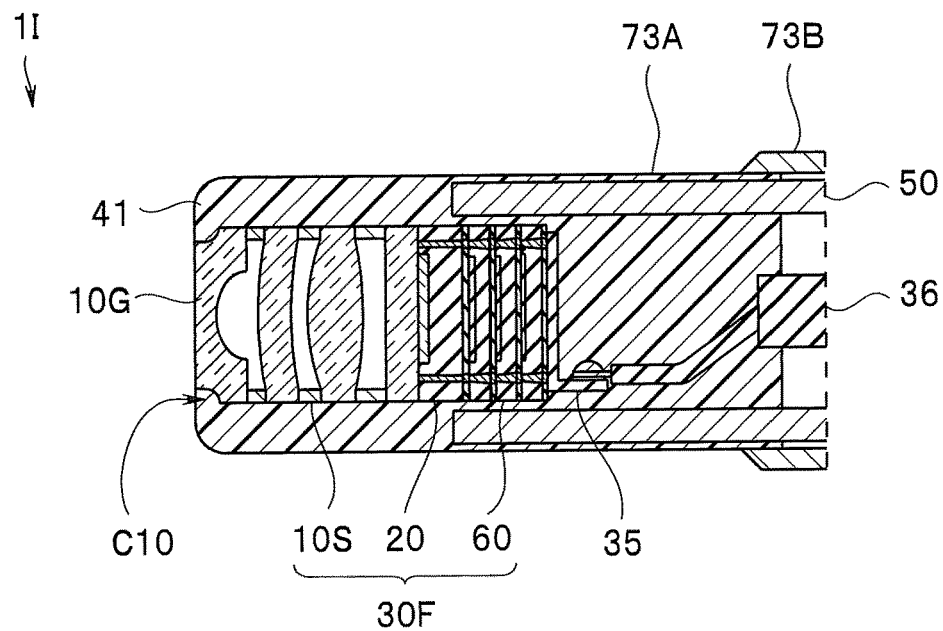
FIG. 27 is a cross-sectional view of a distal end portion of an endoscope according to an eighth embodiment.

As illustrated in FIG. 27, in the endoscope 1I, entirety of an image pickup module 30F is completely housed inside a casing 41 including a mold resin. Then, a maximum length G of a cross-section of each of spaces over side faces of an image pickup module 30F, in which end portions of an operation wire 50, which is a drive member, are fixed, is no less than 100% and no more than 112.5% of an outer dimension of the fixed end. Furthermore, a stepped portion C10 is provided in an outer peripheral portion of a frontmost optical member 10G in an optical module section 10S, and the mold resin of the casing 41 is charged in the stepped portion C10.

It should be understood that an endoscope according to an embodiment of the present invention is not limited to a medical endoscope and may be an industrial endoscope.

The present invention is not limited to the above-described embodiments and modifications and the like, and various changes, combinations and applications are possible without departing from the spirit of the invention.

What is claimed is:

1. An endoscope comprising an insertion portion that includes a distal end portion, and a bending portion configured to change a direction of the distal end portion, the bending portion being provided so as to extend from the distal end portion, wherein:
    the distal end portion includes a casing having a round shape in a cross-section, and an image pickup module that includes an optical module section including a plurality of optical members and an image pickup sensor, the image pickup module having a rectangular shape in a cross-section;
    the image pickup module includes a semiconductor stack in which a plurality of semiconductor devices is stacked;
    an entirety of the image pickup module is completely housed inside the casing;
    an end of an operation wire configured to bend the bending portion is fixed in a space over a side face of the image pickup module; and
    a maximum length of a cross-section of the space is no less than 100% and no more than 112.5% of an outer dimension of the fixed end;
    the operation wire having a round shape in a cross-section; and
    a diameter $R50$ of the operation wire, a length $D30$ of the image pickup module and a diameter $R40$ of the casing meet the following expression:
    $$(R50+D30+R50) \leq R40 \leq 1.25 \times (R50+D30+R50).$$

2. The endoscope according to claim 1, wherein the end of the operation wire is fixed to the side face of the image pickup module.

3. The endoscope according to claim 1, wherein the end of the operation wire is fixed to an inner face of the casing having a cylindrical shape.

4. The endoscope according to claim 1, wherein:
    the casing is formed of a molded resin in which the image pickup module is embedded; and
    the end of the operation wire is embedded in the molded resin.

5. The endoscope according to claim 1, wherein the image pickup module is a wafer-level stack.

6. The endoscope according to claim 1, wherein an outer diameter of the casing is less than 1 mm.

7. The endoscope according to claim 4, wherein an outer peripheral portion of a distal most optical member of the plurality of optical members includes a stepped portion, and molded resin covering an outer peripheral face of the optical module section is filled in the stepped portion.

8. The endoscope according to claim 1, wherein a material of the casing is a light-shielding member.

9. The endoscope according to claim 4, wherein the molded resin includes a light-shielding material.

* * * * *